US008962604B2

(12) United States Patent
Greensmith et al.

(10) Patent No.: US 8,962,604 B2
(45) Date of Patent: Feb. 24, 2015

(54) USE OF A HYDROXIMIC ACID HALIDE DERIVATIVE IN THE TREATMENT OF NEURODEGENERATIVE DISEASES

(75) Inventors: Linda Greensmith, London (GB); Geoffrey Burnstock, London (GB); Rudolf Urbanics, Budapest (HU)

(73) Assignee: Orphazyme ApS, Copenhagen (DK)

( * ) Notice: Subject to any disclaimer, the term of this patent is extended or adjusted under 35 U.S.C. 154(b) by 0 days.

(21) Appl. No.: 13/229,862

(22) Filed: Sep. 12, 2011

(65) Prior Publication Data

US 2012/0115908 A1    May 10, 2012

Related U.S. Application Data

(63) Continuation of application No. 10/582,124, filed as application No. PCT/HU2004/000098 on Oct. 25, 2004, now abandoned.

(30) Foreign Application Priority Data

Oct. 30, 2003    (HU) ..................................... 0303584

(51) Int. Cl.
*A61K 31/33*     (2006.01)
*A61K 31/4545*   (2006.01)

(52) U.S. Cl.
CPC .................. *A61K 31/4545* (2013.01)
USPC ....................................................... 514/183

(58) Field of Classification Search
USPC ....................................................... 514/183
See application file for complete search history.

(56) References Cited

U.S. PATENT DOCUMENTS

| | | | |
|---|---|---|---|
| 4,404,384 A | 9/1983 | Gebert et al. | |
| 5,147,879 A | 9/1992 | Nagy et al. | |
| 5,239,077 A | 8/1993 | Bertok et al. | |
| 5,278,309 A | 1/1994 | Bertok et al. | |
| 5,296,606 A | 3/1994 | Nagy et al. | |
| 5,328,906 A | 7/1994 | Nagy et al. | |
| 5,334,600 A | 8/1994 | Van Duzer et al. | |
| 6,649,628 B1 | 11/2003 | Kurthy et al. | |
| 6,653,326 B1 | 11/2003 | Vigh et al. | |

FOREIGN PATENT DOCUMENTS

| | | |
|---|---|---|
| EP | 1020187 | 7/2000 |
| GB | 1540028 | 2/1979 |
| GB | 1582029 | 12/1980 |
| WO | WO-9004584 | 5/1990 |
| WO | WO-9008131 | 7/1990 |
| WO | WO-9530649 | 11/1995 |
| WO | WO-9713504 | 4/1997 |
| WO | WO-9716439 | 5/1997 |
| WO | WO-9806400 | 2/1998 |
| WO | WO-9843948 | 10/1998 |
| WO | WO-0014054 | 3/2000 |
| WO | WO-0050403 | 8/2000 |
| WO | WO-0179174 | 10/2001 |
| WO | WO-03026653 | 4/2003 |
| WO | WO-03049692 | 6/2003 |

OTHER PUBLICATIONS

Benn et al., "Putting the heat on ALS," Nature Medicine, 10(4):345-347 (2004).
Bruening et al., "Up-regulation of protein chaperones preserves viability of cells expressing toxic Cu/Zn-superoxide dismutase mutants associated with amyotrophic lateral sclerosis," Journal of Neurochemistry, 72(2):693-699 (1999).
Cheung et al., "Selecting promising ALS therapies in clinical trials," Neurology, 67(10):1748-1751 (2006).
Csardi et al., "Pharmacokinetic study on a new antiischaematic agent (BRLP-42)", Acta Physiologica Hungarica, 82(4):321-326 (1994).
European Extended Search Report; Aug. 28, 2009, European Application 08157425.3.
International Search Report, Feb. 28, 2005, PCT Publication WO 2005/041965.
Kalmar et al., "Upregulation of heat shock proteins rescues motoneurones from axotomy-induced cell death in neonatal rats," Experimental Neurology, 176(1):87-97 (2002).
Kieran et al., "Treatment with arimoclomol, a coinducer of heat shock proteins, delays disease progression in ALS mice," Nature Medicine, 10(4):402-405 (2004).
Kurthy et al., "Effect of BRX-220 against peripheral neuropathy and insulin resistance in Diabetic rat models," Annals of the New York Academy of Sciences, 967:482-489 (2002).
Love, "Arimoclomol delays progression in ALS mouse model," Lancet Neurology, 3(5):264 (2004).
Sorensen et al., "Soluble Expression of Recombinant Proteins in the Cytoplasm of *Escherichia coli*," Microbial Cell Factories 4: 1-8(2005).
Toth et al., "Effect of bimoclomol 1 (N-(2-hydroxy-3-(1-piperidinyl) propoxy)-3 pyridine-carboximidoyl-chloride) on iminodipropionitrile-induced central effects," Neurochemistry International, 33(6):513-518 (1998).
Visy et al., "Enantioselective Plasma Protein Binding of Biomoclomal," Chirality, 14:638-642 (2002).
Kalmar et al., "The effect of treatment with BRX-220, a co-inducer of heat shock proteins, on sensory fibers of the rat following peripheral nerve injury"; Experimental Neurology 184 (2003) 636-647.
Kalmar et al., "Activation of the Heat Shock Response in a Primary Cellular Model of Motoneuron Neurodegeneration—Evidence for Neuroprotective and Neurotoxic Effects"; Cellular & Molecular Biology Letters, vol. 14 (2009) pp. 319-335.
Kalmar et al., "Late stage treatment with arimoclomol delays disease progression and prevents protein aggregation in the SOD1G93A mouse model of ALS"; Journal of Neurochemisty 2008, 107, 339-350.

(Continued)

*Primary Examiner* — Wu-Cheng Winston Shen
*Assistant Examiner* — Christopher R Stone
(74) *Attorney, Agent, or Firm* — Gifford, Krass, Sprinkle, Anderson & Citkowski, P.C.

(57) ABSTRACT

The invention relates to the use of a chemical substance selected from the group consisting of N-'2-hydroxy-3-(1-piperidinyl)-propoxyl 1-pyridine-1-oxide-3-carboximidoyl chloride, the optically active enantiomers and the mixtures of enantiomers thereof and pharmaceutically acceptable salts of the racemic and optically active compounds in the preparation of a pharmaceutical composition for the treatment or prevention of neurodegenerative diseases.

6 Claims, No Drawings

(56) References Cited

OTHER PUBLICATIONS

Kelly et al., "Neuroprotection: Heat Shock Proteins," Current Medical Research and Opinion®, vol. 18, Suppl. 2, 2002, s55-60.

Magrané et al., "Heat Shock Protein 70 Participates in the Neuroprotective Response to Intracellularly Expressed β-Amyloid in Neurons," The Journal of Neuroscience, Feb. 18, 2004, 24(7):1700-1706.

Rokutan, Clinician, 45(3):310-313 (1998), English translation attached.

Rakonczay et al., "Nontoxic Heat Shock Protein Coinducer BRX-220 Protects Against Acute Pancreatitis in Rats"; Free Radical Biology & Medicine, vol. 32, No. 12, pp. 1283-1292, 2002.

Šeböková et al., "Comparison of the Extrapancreatic Action of BRX-220 and Pioglitazone in the High-Fat Diet-Induced Insulin Resistance"; Ann. N.Y. Acad. Sci. 967: 424-430 (2002).

Bowling, A. et al., Bioenergetic and Oxidative Stress in neurodegenerative Diseases, *Life Sciences*, 56(14): 1151-71, 1995.

Marber, M. et al., Overexpression of the Rat Inducible 70-kD Heat Stress Protein in a Transgenic Mouse Increases the Resistance of the Heart to ischemic Injury, *J. Clin. Invest*, 95:1446-56, Apr. 1995.

Mestril, R. et al., Heat Shock Proteins and Protection Against Myocardial Ischemia, *J. Mol. Cell. Cardiol*, 27: 45-52, 1995.

Vigh, L. et al., Bimoclomol: A nontoxic, hydroxylamine derivative with stress protein-inducing activity and cytoprotective effects, *Nature Medicine*, 3(10): 1150-54, Oct. 1997.

Cudkowicz, M. et al., Arimoclomol at Dosages up to 300 mg/day is Well Tolerated and Safe in Amyotrophic Lateral Sclerosis, *Muscle & Nerve*, pp. 837-844, Jul. 2008.

Qureshi, M. et al., The natural history of ALS is changing: Improved survival, *Amyotrophic Lateral Sclerosis*, 10: 324-31, 2009.

Arnst, C., Biogen ALS Failure Highlights Clinical Trial Frustrations, Jan. 10, 2013.

Liu, J. et al., Elevation of the Hsps70 chaperone does not affect toxicity in mouse models of familial amyotrophic lateral sclerosis, *J. Neurochem.*, 93(4): 875-82, May 2005 (Abstract).

Report GDHC019POA, Section 7.2 Clinical Trial Design, GlobalData Report Store, published Jun. 2014.

USE OF A HYDROXIMIC ACID HALIDE DERIVATIVE IN THE TREATMENT OF NEURODEGENERATIVE DISEASES

This application is a continuation of U.S. patent application Ser. No. 10/582,124, filed May 10, 2007, which is a national stage application under 35 U.S.C. §371 of International Patent Application PCT/HU04/00098, filed Oct. 25, 2004, which claims priority from Hungarian Patent Application 0303584, filed Oct. 30, 2003. The disclosure of each of these applications is incorporated by reference herein in its entirety.

TECHNICAL FIELD

The present invention relates to the use of N-[2-hydroxy-3-(1-piperidinyl)-propoxy]-pyridine-1-oxide-3-carboximidoyl chloride in the treatment of neurodegenarative diseases.

BACKGROUND ART

As it is known, neurodegenerative diseases are progressive, devastating, chronic age related disorders. With increasing life expectancy the incidence of these age-related diseases will be dramatically increasing in the next decades. The treatment of these maladies currently is only symptomatic, causal therapy does not exist due to the largely unknown cause(s) of these multietiological diseases. Though the etiology and the actual localization of cell damage and loss in the central nervous system (CNS) in these disorders—like Alzheimer's disease (AD), Parkinson's disease (PD), Multiple sclerosis (MS), Neuropathies, Huntington's disease (HD), Amyotrophic lateral sclerosis (ALS)—may differ, there are many common points in the disease development, and in the intracellular events.

Although great progress has been made in the symptomatic treatment of a number of neurodegenerative disorders, there is still a huge, unmet need for pharmacological and biopharmacological treatments that will slow and possibly halt the progress of these diseases.

AD is the most common neurodegenerative disease and the most common form of dementia (responsible for about 80% of all cases). AD is characterized by memory loss, language deterioration, impaired visuospatial skills, poor judgment, indifferent attitude, but preserved motor function.

Alzheimer's disease symptoms appearing first as memory decline and, over several years, destroying cognition, personality, and ability to function. Confusion and restlessness may also occur. Amyloid plaques and neurofibrillary tangles in the brain are the distinctive characteristics of the disease, there is also a loss of nerve cells in areas of the brain that are vital to memory and other mental abilities. The disease usually begins after age 60, and risk goes up with age. While younger people also may get Alzheimer's, it is much less common. About 3 percent of men and women ages 65 to 74 have AD, and nearly half of those age 85 and older may have the disease.

There is no cure today for Alzheimer's disease and patients usually live about 8 to 10 years from the time of diagnosis. There are a number of drugs on the market, which may help prevent some symptoms from worsening for a limited time. In addition, some medicines may help control behavioral symptoms of AD.

Presently there are four drugs approved by the FDA to treat the symptoms of mild-to-moderate AD. These medications are known as cholinesterase inhibitors, which research suggests, act to prevent the breakdown of acetylcholine, a brain chemical believed to be important for memory and thinking. Although none of these medications stops the disease itself, they can help delay or prevent symptoms from becoming worse for a limited time and may help maintaining independence for a longer period of time. As the disease progresses, the brain produces less and less acetylcholine, and the medications may eventually lose their effect. Exelon and Reminyle are the most successful and marketed drugs of this class (See: Neurodegenerative Disorders: The world market 2002-207; a Visiongain Report; VISIONGAIN™, 2003; see also: Terry A V and Buccafusco J J: The cholinergic hypothesis of age and Alzheimer's disease related cognitive deficits: recent challenges and their implications for novel drug development; The Journal of pharmacology and experimental therapeutics, 306: 821-27, 2003; and Cummings J L: Use of cholinesterase inhibitors in clinical practice: evidence based recommendations; Am J Geriatr Psychiatry 11: 131-45, 2003.).

Other treatment trials for AD include the Ginko biloba extract—as an antioxidant, but the studies so far do not demonstrate clear efficacy among AD patients.

Nonsteroidal anti-inflammatory agents tested until today did not proved to be effective.

Newly approved in Europe, Ebixa (Memantine), a non-specific NMDA antagonist that is being marketed by Merz and Lundbeck, is set to compete with the reputed gold standard in treatment, Aricept. Clinical trials have yielded positive results thus far (Mintzer J E: The search for better non-cholinergic treatment options for Alzheimer's disease, J Clin Psychiatry 64, suppl 9:18-22, 2003; and Reisberg B et al.: Memantine in moderate to severe Alzheimer's disease, N Engl J Med 348:1333-41, 2003.). Another, until now controversial approach was the immunization as to develop drugs that is able to decreasing amyloid beta production, and clearing the amyloid deposits by immunization.

PD is the second neurodegenerative disorder in incidence and importance. Parkinson's occurs when certain brain cells in an area of the brain known as the substantia nigra die or become impaired. The exact cause of neuronal death is unknown, but oxidative stress and mitochondrial electron transport chain dysfunction—especially the decreased activity of complex I—is widely accepted. These neurons produce an important chemical known as dopamine, a chemical messenger responsible for transmitting signals between the substantia nigra and the corpus striatum.

Symptoms of Parkinson's disease include the followings: tremor, or the involuntary and rhythmic movements of the hands, arms, legs and jaw, is a primary feature. Classically, tremor appears while the individual is at rest and improves with intentional movement; Gradual loss of spontaneous movement, which often leads to a variety of problems such as "freezing", decreased mental skill or quickness, voice changes, and decrease facial expression; Muscle rigidity, or stiffness of the limbs, occurs in all muscle groups but is most common in the arms, shoulders or neck; Postural instability, or a stooped, flexed posture with bending at the elbows, knees and hips; Gradual loss of automatic movement, including eye blinking and decreased frequency of swallowing; Unsteady walk; Depression and dementia.

Patients of the disease currently have a large number of treatment options and this number will also be rising steadily over the next 10 to 15 years. The first effective therapy for the treatment of Parkinson's, carbidopa/levodopa (Sinemet-Bristol Myers Squibb), was introduced in 1970 and revolutionized treatment of the disease. The therapy proved very effective in controlling symptoms such as tremor, bradykinesia, balance, and rigidity. However, dyskinetic side-effects and reduced effect with prolonged treatment proved the need for alternative treatments and/or ancillary drugs to offset side-effects. Dopamine agonists, which entered the market in the 1980s, filled this need. These drugs have proved effective as a type of dopamine regulator and as a monotherapy in delaying the need for carbidopa/levodopa therapy in newly diagnosed Parkinson's patients. Other newly developed therapies such as COMT inhibitors, anticholinergics, and selegiline/deprenyl have also had an effect, although less marked, on the PD market (See: Neurodegenerative Disorders: The world market 2002-207; a Visiongain Report; VISIONGAIN™, 2003.).

Amyotrophic lateral sclerosis (ALS), sometimes called Lou Gehrig's disease, is a rapidly progressive, invariably fatal neurological disease that attacks the nerve cells (neurons) responsible for controlling voluntary muscles. The disease is the most common motor neuron disease, which is characterized by the gradual degeneration and death of motor neurons (Rowland L P, Schneider N A: Amyotrophic lateral sclerosis. N Engl J Med 344:1688-1700, 2001.). Motor neurons are nerve cells located in the brain, brainstem, and spinal cord that serve as controlling units and vital communication links between the nervous system and the voluntary muscles of the body. Messages from motor neurons in the brain (called upper motor neurons) are transmitted to motor neurons in the spinal cord (called lower motor neurons) and from them to particular muscles. In ALS, both the upper motor neurons and the lower motor neurons degenerate or die, ceasing to send messages to muscles. Unable to function, the muscles gradually weaken, waste away (atrophy), and twitch (fasciculations). Eventually, the ability of the brain to start and control voluntary movement is lost. Most people with ALS die from respiratory failure, usually within 3 to 5 years from the onset of symptoms.

The cause of ALS is not known. However, an important step toward answering that question came in 1993 when scientists discovered that mutations in the gene that produces the SOD1 enzyme were associated with some cases of familial ALS (Rosen D R et at: Mutations in Cu/Zn superoxide dismutase gene are associated with familial amyotrophic lateral sclerosis. Nature, 362: 59-62, 1993.). This enzyme is a powerful antioxidant that protects the body from damage caused by free radicals. Free radicals are highly unstable molecules produced by cells during normal metabolism (the major source is the mitochondrion). If not neutralized, free radicals can accumulate and cause random damage to the DNA, membrane lipids and proteins within cells. Although it is not yet clear how the SOD1 gene mutation leads to motor neuron degeneration, researchers have theorized that an accumulation of free radicals may result from the faulty functioning of this gene.

Although many distinct features are present in the neurodegenerative diseases, common feature is, the cell loss, gradual and progressive degeneration of certain central nervous system areas. Imbalance in reactive oxygen species (ROS) production and neutralization capacity is increasing with ageing, and neurodegenerative diseases worsen this. The role of SOD in ALS was described above as a powerful antioxidant that protects the brain from damage caused by free radicals. In Parkinson's disease ROS is generated by autooxidation during normal dopamine metabolism or by the action of monoamine oxidase (Lev N et al.: Apoptosis and Parkinson's disease; Progress in Neuro-Psychopharmacology and Biological psychiatry 27: 245-50, 2003.). In AD the exact initiating events leading to disease development are complex, but it is widely accepted that neuronal death is mediated partly by free radical injury (Pratico D and Delanty N: Oxidative injury in diseases of the central nervous system: Focus on Alzheimer's disease, Am J Med 109: 577-85, 2000.)

Currently the only proven therapy for patients suffering from ALS, Riluzole, extents survival by approximately 3 months. (Miller, R. G., Mitchell, J. D., Lyon, M. & Moore, D. H. Riluzole for amyotrophic lateral sclerosis (ALS)/motor neuron disease (MND). Cochrane. Database. Syst. Rev. CD001447 (2002)). Therefore, the identification of new therapeutic strategies to employ for the treatment of ALS remains a priority.

It is known from WO 97/16439 that several types of hydroxylamine derivatives enhance chaperon expression in cells exposed to a physiological stress and are useful in the treatment of diseases connected with the function of chaperon system. Various new categories of hydroxylamine derivatives are disclosed in this published patent application. A certain class of hydroximic acid halides N-[2-hydroxy-3-(1-piperidinyl)-propoxy]-pyridine-1-oxide-3-carboximidoyl chloride belongs to is also defined but N-[2-hydroxy-3-(1-piperidinyl)-propoxy]-pyridine-1-oxide-3-carboximidoyl chloride is not mentioned explicitly.

N-[2-hydroxy-3-(1-piperidinyl)-propoxy]-pyridine-1-oxide-3-carboximidoyl chloride is first disclosed and claimed in WO 00/50403 as an eminent species capable of lowering insulin resistance. As stated, it is useful in the treatment of a series of chronic diabetic complications especially rethinopathy, neuropathy and nephropathy and pathological decrease of neuroregeneration caused by diabetes while reducing insulin resistance in the patient. The chemical properties of this compound and details of the synthetic procedure of its preparation are also described in the said paper.

An other utility of N-[2-hydroxy-3-(1-piperidinyl)-propoxy]-pyridine-1-oxide-3-carboximidoyl chloride in diabetic therapy especially in the therapy of type II (non-insulin dependent, NIDDM) diabetes is described in WO 03/026653.

The invention disclosed here relates to an orally applicable antihyperglycemic composition containing a combination of metformin and N-[2-hydroxy-3-(1-piperidinyl)-propoxy]-pyridine-1-oxide-3-carboximidoyl chloride as active principle. The outstanding antihyperglycemic effect is based on synergism deriving from the combination of the two active agents.

None of the patent publications relating to N-[2-hydroxy-3-(1-piperidinyl)-propoxy]-pyridine-1-oxide-3-carboximidoyl chloride suggests the use of this compound outside of the diabetes therapy.

DISCLOSURE OF INVENTION

We have found that N-[2-hydroxy-3-(1-piperidinyl)-propoxy]-pyridine-1-oxide-3-carboximidoyl chloride has biological properties making it useful in the therapy of neurodegenerative diseases. In a research study, conducted on mSOD1$^{(G93A)}$ transgenic mice, N-[2-hydroxy-3-(1-piperidinyl)-propoxy]-pyridine-1-oxide-3-carboximidoyl chloride prevented the progressive loss of motoneurons and muscle function that normally occurs in this mouse model of ALS.

Based on the above recognition the invention provides a new use of N-[2-hydroxy-3-(1-piperidinyl)-propoxy]-pyridine-1-oxide-3-carboximidoyl chloride in the preparation of pharmaceutical compositions for the treatment or prevention of neurodegenerative diseases.

Preferably, the invention provides a new use of N-[2-hydroxy-3-(1-piperidinyl)-propoxy]-pyridine-1-oxide-3-carboximidoyl chloride in the preparation of pharmaceutical compositions for the treatment or prevention of amyotrophic lateral sclerosis.

Further, the invention provides a method of treatment or prevention of neurodegenerative diseases wherein a therapeutically effective amount of N-[2-hydroxy-3-(1-piperidinyl)-propoxy]-pyridine-1-oxide-3-carboximidoyl chloride is administered to a patient.

Preferably, the invention provides a method of treatment or prevention of amyotrophic lateral sclerosis wherein a therapeutically effective amount of N-[2-hydroxy-3-(1-piperidinyl)-propoxy]-pyridine-1-oxide-3-carboximidoyl chloride is administered to a patient.

In respect of the invention the term N-[2-hydroxy-3-(1-piperidinyl)-propoxy]-pyridine-1-oxide-3-carboximidoyl chloride relates to N-[2-hydroxy-3-(1-piperidinyl)-propoxy]-pyridine-1-oxide-3-carboximidoyl chloride as a free base, a pharmaceutically acceptable acid addition salt thereof formed with a mineral or organic acid as well as the racemic compound and each of the optically active enantiomers and mixtures of enantiomers and pharmaceutically acceptable salts of the optically active enantiomers or enantiomer mixtures.

It is to be remarked that N-[2-hydroxy-3-(1-piperidinyl)-propoxy]-pyridine-1-oxide-3-carboximidoyl chloride is preferably used in form of an acid addition salt. It is to be remarked further that optically active forms of this compound are preferable, especially (+)-R—N-[2-hydroxy-3-(1-piperidinyl)-propoxy]-pyridine-1-oxide-3-carboximidoyl chloride. More preferable are the acid addition salts of the latter optically active enantiomer and the most preferable one is (+)-R—N-[2-hydroxy-3-(1-piperidinyl)-propoxy]-pyridine-1-oxide-3-carboximidoyl chloride citrate.

The term "neurodegenerative disease" refers to known types of neurodegenerative diseases including amyotrophic lateral sclerosis (ALS), Alzheimer's disease (AD), Parkinson's disease (PD), Huntington's disease (HD) multiple sclerosis (MS), and various types of neuropathies.

BEST MODE OF CARRYING OUT THE INVENTION

The following biological tests were carried out with (+)-R—N-[2-hydroxy-3-(1-piperidinyl)-propoxy]-pyridine-1-oxide-3-carboximidoyl chloride citrate as a test compound. This chemical compound will be referred to as compound A.

Transgenic mSOD1$^{(G93A)}$ mice of both sexes were used in this study. All experimental animals were treated daily with compound A (10 mg/kg, i.p.) from 35 days of age, following a similar regime to that previously described by Zhu et al 2002 (Zhu, S. et al. Minocycline inhibits cytochrome c release and delays progression of amyotrophic lateral sclerosis in mice. Nature 417, 74-78 (2002)).

Assessment of Muscle Function and Motor Unit Number

Live, in-vivo electrophysiological assessment of hind limb muscle function was carried out on the extensor digitorum longus (EDL) muscles in both hind limbsto determine the extent of disease progression. Isometric tension recordings and assessment of motor unit number.

Both transgenic animals and their wildtype littermates were anaesthetized with chloral hydrate (4% chloral hydrate; 1 ml/100 g body weight, i.p.), and the EDL muscles were prepared for in vivo assessment of their contractile properties and motor unit number. The distal tendons of the EDL muscles were dissected and attached to isometric force transducers (Dynamometer UFI Devices) via silk threads. Both legs were rigidly secured to the table with pins. The sciatic nerve was dissected free, and all its branches, apart from the nerve to the EDL muscle were cut. The distal end of the nerve was then stimulated using bipolar silver electrodes. The length of the muscle was adjusted until the maximal twitch was produced upon nerve stimulation. Isometric contractions were elicited by stimulating the cut end of the motor nerve using a pulse width of 0.02 ms. Tetanic contractions were elicited by stimulating the EDL muscle at 40, 80 and 100 Hz for 500 ms.

To estimate the number of motor units in each muscle, the motor nerves of the EDL muscles were stimulated every 4 s. The stimulus strength was gradually increased to obtain stepwise increments of twitch tensions, as individual motor axons were recruited. The number of stepwise increments was counted to give an estimate of the number of motor units present in each muscle.

(Dick, J., Greensmith, L. & Vrbova, G. Blocking of NMDA receptors during a critical stage of development reduces the effects of nerve injury at birth on muscles and motoneurones. Neuromuscul. Disord. 5, 371-382 (1995)).

From recordings of twitch tension we assessed some of the contractile characteristics of EDL muscles in treated and untreated mSOD1$^{(G93A)}$ transgenic mice including the half relaxation time of EDL, a measure of the time it takes for the muscle to relax after contraction.

Fatigue Pattern

Since EDL is normally a fast muscle it fatigues quickly when continuously stimulated to produce a characteristic fatigue pattern. To examine the fatigue pattern of EDL in these experiments, the muscles in both hind limbs were stimulated at 40 Hz for 250 ms, every second for 3 minutes and muscle contractions were recorded.

Muscle Histology

At the end of the experiment the EDL muscles in both legs were removed and weighed, and snap frozen in melting isopentane. The muscles were stored at –80° until processing for histological analysis.

Assessment of Motoneuron Survival

Following completion of the physiological experiments, motoneuron survival was assessed by counting the number of motoneurons in the sciatic motor pool in the ventral horns from cross sections of lumbar spinal cord. (White, C. M., Greensmith, L. & Vrbova, G. Repeated stimuli for axonal growth causes motoneuron death in adult rats: the effect of botulinum toxin followed by partial denervation. Neuroscience 95, 1101-1109 (2000)). The mice were deeply anaesthetized (4% chloral hydrate, 1 ml/100 g body weight, ip.) and perfused transcardially with a fixative containing 4% paraformaldehyde. The spinal cords were removed and the lumbar region postfixed for 2 h in the same fixative, cryoprotected in sucrose (30% in MPB) and frozen transverse sections cut on a cryostat at 30 µm and collected onto subbed slides. The sections were then lightly counterstained with a Nissl stain (gallocyanin). The number of Nissl stained motoneurons in both ventral horns was counted under a light microscope. In order to avoid counting the same cell twice in consecutive sections, motoneuron survival was assessed in the sciatic motor pool in every $3^{rd}$ section of the lumbar region of the spinal cord between levels L2-L5. Only those neurons in which the nucleolus was clearly visible at high magnification were included in the counts.

Statistical Analysis

For all parameters assessed, the results were analyzed using the Mann-Whitney U-test for comparison of independent samples. Two-tailed tests were used in all instances, and significance was set at P<0.05.

Results

At 35 days of age mSOD1$^{(G93A)}$ transgenic mice already show microscopic features of lumbar motoneuron degeneration, and by 110 days of age hind limb paralysis is manifest. The effect of treatment with compound A on hind limb muscle function as well as motor unit and motoneuron survival was assessed at 120 days of age when mSOD1$^{(G93A)}$ transgenic mice are in the later stage of the disease.

Motor Unit Survival

In wild-type mice there are normally 28+/−0.6 (mean+/−S.E.M., n=11) motor units in EDL muscles. In mSOD1$^{(G93A)}$ transgenic mice at 120 days of age there were only 8.3+/−0.7 (mean+/−S.E.M., n=10) motor units. However, in mSOD1$^{(G93A)}$ transgenic mice treated with compound A there is a significant improvement in motor unit survival, and 14.3+/−0.6 (mean+/−S.E.M., n=10) motor units survived at 120 days of age (p=0.003).

Contractile Characteristics of EDL Muscles i) Half Relaxation Time of EDL Muscles From recordings of twitch tension we also examined some of the contractile characteristics of EDL muscles in treated and untreated mSOD1$^{(G93A)}$ transgenic mice. EDL is normally a fast, fatigable muscle and in wild-type mice the half relaxation time of EDL, a measure of the time it takes for the muscle to relax after contraction, is 25.8 ms+/−2.4 (mean+/−S.E.M., n=10). In contrast, in untreated mice, the half relaxation time slows as a consequence of denervation and muscle atrophy and was found to be 43.3 ms+/−6.93 (mean+/−S.E.M., n=10). However, in mice treated with compound A the half relaxation time was significantly improved, and was found to be 32.2 ms+/−1.80 (mean+/−S.E.M., n=10), (p=0.030).

ii) Fatigue Pattern and Fatigue Index of EDL Muscles

Since EDL is normally a fast muscle it fatigues quickly when continuously stimulated to produce a characteristic fatigue pattern. The fatigue pattern of EDL muscles was examined in wild type, mSOD1$^{(G93A)}$ transgenic and treated mSOD1$^{(G93A)}$ transgenic mice. The decrease in tension after 3 minutes of stimulation was measured and a fatigue index (FI) calculated. In mSOD1$^{(G93A)}$ transgenic mice at 120 days of age the EDL muscle becomes fatigue resistant as a result of motoneuron degeneration, denervation and consequent changes in muscle fibre phenotype. Thus, in mSOD1$^{(G93A)}$ transgenic mice at 120 days of age EDL has a fatigue index of 0.255+/−0.04 (mean+/−S.E.M., n=10), compared to 0.848+/−0.028 (mean+/−S.E.M, n=10) in wild-type mice. However, in mice treated with compound A EDL has a fatigue index of 0.416+/−0.07 (mean+/−S.E.M., n=10). Thus, the fatigue index of EDL was significantly improved in treated mSOD1$^{(G93A)}$ transgenic mice compared to untreated mSOD1$^{(G93A)}$ littermates (p=<0.05).

Motoneuron Survival

Following completion of the physiological experiments, motoneuron survival was assessed by counting the number of motoneurons in the sciatic motor pool in the ventral horns from cross sections of lumbar spinal cord.

Corresponding with the increase observed in motor unit survival, the number of motoneurons surviving in the sciatic motor pool of treated mSOD1$^{(G93A)}$ transgenic mice was also significantly increased compared to their untreated-mSOD1$^{(G93A)}$ littermates. In wild-type mice there were 593+/−15.8 (mean+/−S.E.M., n=13) motoneurons in the segment of the sciatic motor pool examined. In untreated mSOD1$^{(G93A)}$ transgenic mice at 120 days of age a significant number of motoneurons have died, and only 237+/−14 (mean+/−S.E.M., n=7) motoneurons survive. However, in mSOD1$^{(G93A)}$ transgenic mice treated with compound A, there is a dramatic increase in motoneuron survival with 412+/−28 (mean+/−S.E.M., n=4) motoneurons surviving, even at 120 days of age (p=0.002).

These results show that following daily treatment of mSOD1$^{(G93A)}$ transgenic mice with compound A (10 mg/kg; i.p.) there is a significant increase in both motor unit and motoneuron survival, as well as an improvement in hind limb muscle function in the later stages of the disease (120 days).

Life Span

In view of the significant improvements in motor unit number and motoneuron survival observed in treated mSOD1$^{(G93A)}$ transgenic mice at 120 days of age, in a separated group of mice we examined whether treatment with compound A would have an effect on the lifespan of mSOD1$^{(G93A)}$ transgenic mice. We found that untreated mSOD1$^{(G93A)}$ transgenic mice had an average lifespan of 125+/−1.8 (mean+/−S.E.M., n=18) days, as determined by both an inability of the mouse to right itself when put on its side and the loss of approximately 20% body weight. However, in the group treated with compound A the decline in body weight was delayed and lifespan was significantly improved, and mSOD1$^{(G93A)}$ mice lived on average for 153+/−2.6 (mean+/−S.E.M., n=7) days. This represents a significant increase in lifespan of over 22% (p=<0.001).

The above biological properties make N-[2-hydroxy-3-(1-piperidinyl)-propoxy]-pyridine-1-oxide-3-carboximidoyl chloride useful in the treatment of neurodegenerative diseases. Although all kinds of neurodegenerative diseases can be taken into account, the compound of the invention is particularly useful in the treatment of ALS. The dose of the compounds depends on the condition and the illness of the patient, and the daily dose is 0.1-400 mg/kg, preferably 0.1-100 mg/kg body weights. In human therapy, the oral daily dose is preferably 10-300 mg. These doses are administered in unit dosage forms, which may be divided into 2-3 smaller doses for each day in certain cases, especially in oral treatment.

Preferably, the stereoisomer of the racemic compound, most preferably the (+) enantiomer is used. In this case, a smaller quantity of active ingredient within the above limits will be sufficient for the treatment.

The active substance can be formulated into the usual pharmaceutical compositions in a manner known in the art. These pharmaceutical compositions contain, in addition to the usual auxiliary substances and carriers, N-[2-hydroxy-3-(1-piperidinyl)-propoxy]-pyridine-1-oxide-3-carboximidoyl-chloride or one of its stereoisomers, or an acid addition salt of one of them, as active ingredients.

The pharmaceutical compositions can be prepared in the form of a solid or fluid preparation generally used in the therapy. Simple or coated tablets, dragées, granulates, capsules, solutions or syrups can be prepared for oral administration. These medicines can be produced by the usual methods. The products can contain filling materials such as microcrystalline cellulose, starch or lactose, lubricants such as stearic acid or magnesium stearate, coating materials such as sugar, film forming materials such as hydroxy-methylcellulose, aromas or sweeteners such as methyl-paraben or saccharine, or coloring substances.

The invention claimed is:

1. A method of treating a patient with amyotrophic lateral sclerosis, said method comprising administering a therapeutically effective amount of (+)-R—N-[2-hydroxy-3-(1-piperidinyl)-propoxy]-pyridine-1-oxide-3-carboximidoyl chloride citrate to said patient having amyotrophic lateral sclerosis.

2. The method of claim 1, wherein (+)-R—N-[2-hydroxy-3-(1-piperidinyl)-propoxy]-pyridine-1-oxide-3-carboximidoyl chloride citrate is administered as a daily dose of 0.1-400 mg/kg.

3. The method of claim 1, wherein (+)-R—N-[2-hydroxy-3-(1-piperidinyl)-propoxy]-pyridine-1-oxide-3-carboximidoyl chloride citrate is administered as a daily dose of 0.1-100 mg/kg.

4. The method of claim 1, wherein (+)-R—N-[2-hydroxy-3-(1-piperidinyl)-propoxy]-pyridine-1-oxide-3-carboximidoyl chloride citrate is administered as an oral daily dose of 10-300 mg.

5. The method according to claim 1, wherein (+)-R—N-[2-hydroxy-3-(1-piperidinyl)-propoxy]-pyridine-1-oxide-3-carboximidoyl chloride citrate is administered at or after motoneuron degeneration onset.

6. The method according to claim 1, wherein said amyotrophic lateral sclerosis is familial amyotrophic lateral sclerosis.

\* \* \* \* \*